United States Patent
Haubrich et al.

(10) Patent No.: US 8,838,251 B2
(45) Date of Patent: Sep. 16, 2014

(54) VARIABLE IMPLANTABLE MEDICAL DEVICE POWER CHARACTERISTICS BASED UPON DATA OR DEVICE TYPE

(75) Inventors: Gregory J. Haubrich, Champlin, MN (US); Javaid Masoud, Shoreview, MN (US); Charles H. Dudding, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 1582 days.

(21) Appl. No.: 11/460,774

(22) Filed: Jul. 28, 2006

(65) Prior Publication Data

US 2008/0027501 A1 Jan. 31, 2008

(51) Int. Cl.
*A61N 1/08* (2006.01)
*A61N 1/372* (2006.01)

(52) U.S. Cl.
CPC .................................. *A61N 1/37276* (2013.01)
USPC .......................................................... 607/60

(58) Field of Classification Search
USPC .............. 607/2, 60, 128, 32, 31, 69; 128/903; 455/69
See application file for complete search history.

(56) References Cited

U.S. PATENT DOCUMENTS

| | | |
|---|---|---|
| 5,476,488 A | 12/1995 | Morgan et al. |
| 5,562,713 A | 10/1996 | Silvian |
| 5,683,432 A * | 11/1997 | Goedeke et al. ................. 607/32 |
| 5,748,103 A | 5/1998 | Flach et al. |
| 5,752,976 A * | 5/1998 | Duffin et al. ..................... 607/32 |
| 5,807,336 A | 9/1998 | Russo et al. |
| 5,843,139 A | 12/1998 | Goedeke et al. |
| 5,944,745 A | 8/1999 | Rueter |
| 6,073,050 A | 6/2000 | Griffith |
| 6,201,993 B1 * | 3/2001 | Kruse et al. ...................... 607/30 |
| 6,766,198 B1 | 7/2004 | Snell |
| 7,065,409 B2 * | 6/2006 | Mazar ............................. 607/60 |
| 7,069,086 B2 | 6/2006 | Von Arx |
| 7,502,594 B2 * | 3/2009 | Ginggen et al. ................. 455/69 |
| 2003/0199939 A1 | 10/2003 | Schmitt et al. |
| 2004/0030260 A1 | 2/2004 | Arx |
| 2005/0197680 A1 | 9/2005 | DelMain et al. |
| 2005/0251579 A1 | 11/2005 | Ngo et al. |
| 2005/0283208 A1 | 12/2005 | Von Arx et al. |
| 2005/0288738 A1 | 12/2005 | Bange et al. |
| 2006/0020301 A1 | 1/2006 | Hanson et al. |
| 2006/0030901 A1 | 2/2006 | Quiles et al. |
| 2007/0123946 A1 | 5/2007 | Masoud |
| 2007/0255318 A1 | 11/2007 | Dudding et al. |

FOREIGN PATENT DOCUMENTS

| | | |
|---|---|---|
| EP | 0607638 A2 | 12/1993 |
| WO | 01/97907 A2 | 12/2001 |
| WO | 2005061048 | 7/2005 |

* cited by examiner

*Primary Examiner* — Paula J Stice
(74) *Attorney, Agent, or Firm* — Michael J. Ostrom; Stephen W. Bauer

(57) ABSTRACT

An implantable medical device ("IMD") as described herein includes adjustable power characteristics such as variable transmitter output power and variable receiver front end gain. These power characteristics can be adjusted in a dynamic manner based upon various operating aspects of the intended or actual IMD telemetry environment. These operating aspects may include the external telemetry device type, the IMD device type, and/or the type, context, or meaning of the telemetry data transmitted by the IMD. The IMD may process information related to these operating aspects to generate power scaling instructions or control signals that are interpreted by the IMD transmitter and/or the IMD receiver. Such adjustability enables the IMD to satisfy minimum telemetry requirements in a manner that does not waste power, thus extending the IMD battery life.

28 Claims, 8 Drawing Sheets

VARIABLE IMPLANTABLE MEDICAL DEVICE POWER CHARACTERISTICS BASED UPON DATA OR DEVICE TYPE

TECHNICAL FIELD

The present invention relates generally to implantable medical devices ("IMDs"). More particularly, the present invention relates to power management techniques for use with IMDs.

BACKGROUND

IMDs are used to treat patients suffering from a variety of conditions. Examples of IMDs involving cardiac devices are implantable pacemakers and implantable cardioverter-defibrillators ("ICDs"). Such electronic medical devices generally monitor the electrical activity of the heart and provide electrical stimulation to one or more of the heart chambers when necessary. For example, pacemakers are designed to sense arrhythmias, i.e., disturbances in heart rhythm, and, in turn, provide appropriate electrical stimulation pulses at a controlled rate to selected chambers of the heart in order to correct the arrhythmias and restore the proper heart rhythm. The types of arrhythmias that may be detected and corrected by IMDs include bradycardias (unusually slow heart rates) and certain tachycardias (unusually fast heart rates).

ICDs also detect arrhythmias and provide appropriate electrical stimulation pulses to selected chambers of the heart to correct the abnormal heart rate. In contrast to pacemakers, however, an ICD can also provide pulses that are much stronger and less frequent, where such pulses are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy therapy pulses to the heart.

Generally, IMDs are equipped with on-board memory in which telemetered signals can be stored for later retrieval and analysis. Typically, the telemetered signals can provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, IMDs store the telemetered signals over a set period of time (usually before, during, and after the occurrence of such arrhythmic event). Current practice in the art involves the use of an external communication unit, e.g., an external programmer, for non-invasive communication with IMDs via uplink and downlink communication channels associated with the communication device. In accordance with conventional medical device programming systems, a programming head can be used for facilitating two-way communication between IMDs and the external communication device. In many known IMD systems, the programming head can be positioned on the patient's body over the IMD side such that the programming head can send wireless signals to, and receive wireless signals from, the IMD in accordance with common practice in the art.

Implementation and operation of most, if not all, RF communication systems for IMDs and external communication devices involves a balancing or compromising of certain countervailing considerations, relating to such interrelated operational parameters as data transmission rate, transmission range, IMD power consumption and battery life, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. For example, to meet a minimum transmission range, the transmitter output power of an IMD must provide telemetry signals having sufficient energy.

Conventional IMDs are limited in that they typically operate with fixed power characteristics. Moreover, power characteristics of a typical IMD are usually set without considering the particular type of external device with which the IMD is currently communicating, without considering the current telemetry communication context for the IMD, and without considering the particular contextual meaning of the data to be transmitted by the IMD. Consequently, such an IMD transmit telemetry signals using more power than is necessary, resulting in wasted transmitter output power and decreased battery life.

Accordingly, it is desirable to have an IMD equipped with variable power characteristics that can be dynamically adjusted in response to certain characteristics of the operating environment and/or the context of the telemetered data. Furthermore, other desirable features and characteristics of the present invention will become apparent from the subsequent detailed description and the appended claims, taken in conjunction with the accompanying drawings and the foregoing technical field and background.

BRIEF SUMMARY

An IMD as described herein can optimize its battery life to suit the particular operating environment and/or according to the contextual meaning of the data to be transmitted or received by the IMD. An IMD as described herein may adjust its power characteristics according to the type of telemetry communication device with which the IMD communicates, according to the IMD type, according to the current telemetry communication context for the IMD, and/or according to the data type communicated between the IMD and the telemetry communication device.

The above and other aspects of the invention may be carried out in one embodiment by a method for operating an IMD. The method involves: obtaining information pertaining to a telemetry communication device for the IMD; performing a power scaling routine for the IMD based upon the information; and adjusting power characteristics of the IMD in response to the power scaling routine.

The above and other aspects of the invention may be carried out in another embodiment by a method for operating an IMD. This method involves: processing IMD device type information for the IMD, the IMD device type information being indicative of a current telemetry communication context for the IMD; performing a power scaling routine for the IMD based upon the IMD device type information; and adjusting power characteristics of the IMD in response to the power scaling routine.

The above and other aspects of the invention may be carried out in yet another embodiment by a method for operating an IMD. This method involves: obtaining contextual meaning information for data to be transmitted via telemetry communication from the IMD; performing a power scaling routine for the IMD based upon the contextual meaning information; and adjusting power characteristics of the IMD in response to the power scaling routine.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
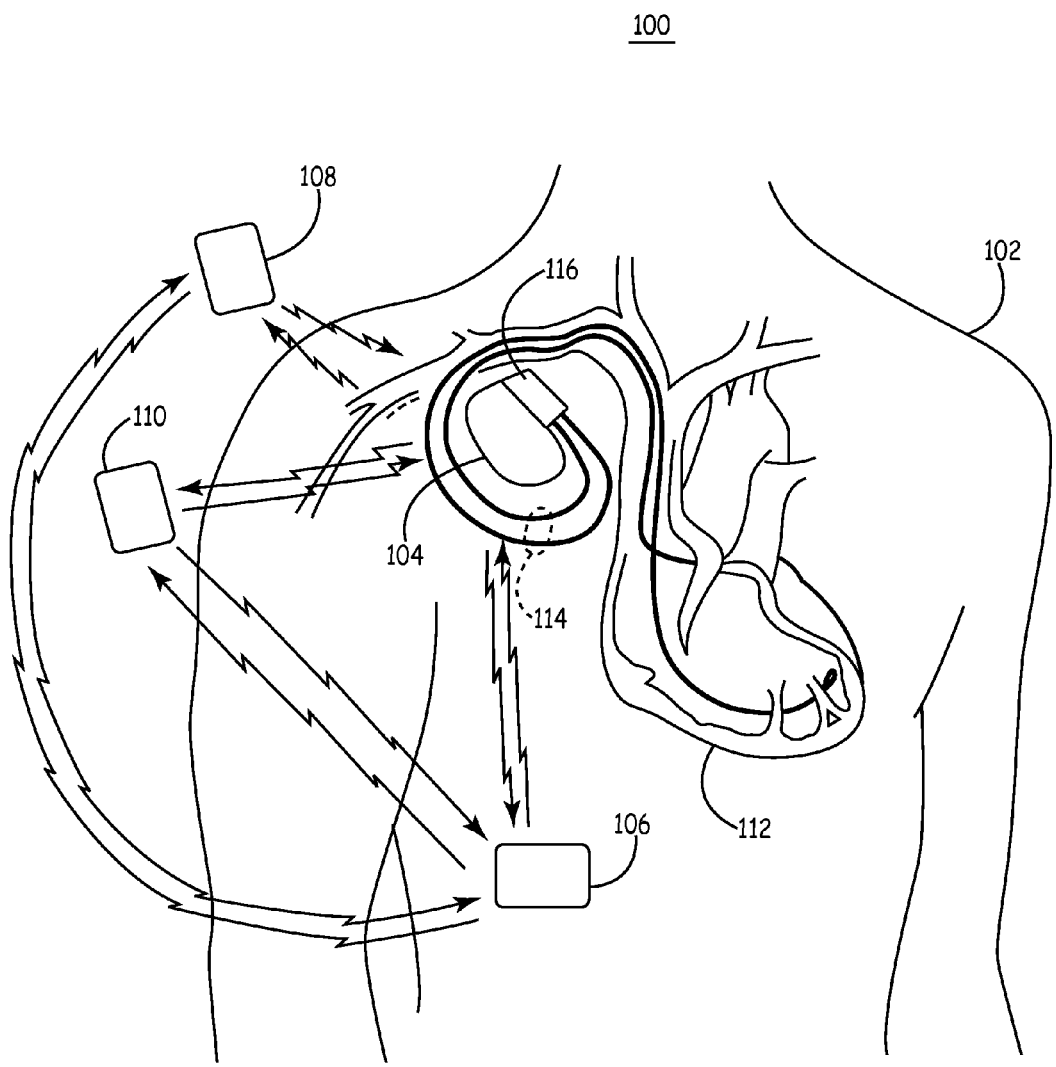
FIG. 1 is an illustration of a system including an IMD in accordance with certain embodiments of the invention.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the system described herein is merely one exemplary application for the invention.

For the sake of brevity, conventional techniques and features related to IMDs, IMD telemetry, signal processing, data transmission, signaling, IMD transceivers, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description refers to elements or features being "connected" or "coupled" together. As used herein, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although the figures may depict example arrangements of elements, additional intervening elements, devices, features, or components may be present in an actual embodiment (assuming that the functionality of the device/system is not adversely affected).

The embodiments of the present invention can be implemented with any IMD having wireless telemetry capabilities. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., artificial hearts). In addition, as the technology advances, it is contemplated that IMDs shall become even more complex with respect to programmable operating modes, menus of operating parameters, and monitoring capabilities of increasing varieties of physiologic conditions and electrical signals. It is to be appreciated that embodiments of the present invention will be applicable in such emerging IMD technology as well. Further, the embodiments of the invention can be implemented in more than one IMD implanted within the same patient to enable telemetry communication between the IMDs.

FIG. 1 illustrates bi-directional telemetry communication involving one or more IMDs in accordance with certain embodiments of the invention. FIG. 1 generally represents a body area network system 100 having multiple devices configured to communicate with one another. As used herein, a "body area network" is a localized network of communicating devices associated with a single patient 102, where devices within the body area network are suitably configured to communicate with each other using one or more data communication protocols. A body area network device may be an IMD, a device affixed to the patient (such as a physiologic characteristic sensor or monitor), a device worn or held by the patient (such as a remote control device for an IMD, a wireless monitor device for an IMD, or a handheld programmer for an IMD), or a device in close proximity to the patient (such as an external programmer that communicates with an IMD). In this example, system 100 generally includes an IMD 104 implanted within patient 102, another IMD 106 implanted within patient 102, and two external communication devices 108/110 that are not implanted within patient 102.

In certain embodiments communications can take place between IMD 104 and any number of the devices within system 100. Moreover, telemetry communications may take place between devices (other than IMD 104) within system 100. The arrows in FIG. 1 represent such telemetry communications. In practice, a given communication session between two devices in system 100 may be unidirectional or bidirectional (in this example, FIG. 1 depicts bidirectional communications). In certain embodiments, the electrical devices can include one or more of at least one implantable medical instrumentation and of at least one external communication device. As shown in FIG. 1, in certain embodiments, the at least one implantable medical instrumentation can include IMD 104 and IMD 106, and the at least one external communication device can include external communication devices 108 and 110; however, it is to be appreciated that such quantities are not provided to limit the scope of application of embodiments of the invention.

In certain embodiments, when IMD 104 is used for cardiac applications (e.g., to provide cardiac sensing and pacing functions for patient 102), IMD 104 can be a cardiac device; for example, a pacemaker, an ICD, a hemodynamic monitor, or the like. As described above, however, neither IMD 104 nor any of the devices within system 100 should be limited to such applications or such devices. In this example, IMDs 104/106 are implanted in the same patient 102 beneath the patient's skin or muscle and, in certain embodiments, IMDs 104/106 can be typically oriented to the skin surface. In certain embodiments, when IMD 104 is used for cardiac applications, as shown, IMD 104 is electrically coupled to the heart 112 of the patient 102 through pace/sense or cardioversion/defibrillation electrodes operatively coupled to lead conductor(s) of one or more endocardial leads 114, which in turn, are coupled to a connector block 116 of IMD 104 in a manner well known in the art.

As generally mentioned above, among other design functions, each of the external communication devices 108/110 is designed for non-invasive communication with one or more of the IMDs 104/106, where such communication is enabled via downlink and uplink communication channels, which will be further described below. In certain embodiments, one or more of the external communication devices 108/110 can be an external pressure reference monitor ("EPR"). An EPR is typically used to derive reference pressure data for use in combination with absolute pressure derived from an IMD. In addition, an EPR measures and records barometric pressure which is necessary for correlation to atmospheric pressure. However, it is to be appreciated that embodiments of the invention are not limited to such EPR applications. Generally, any form of portable programmer, interrogator, recorder, monitor, or telemetered signals transmitter and/or receiver found suitable for communicating with IMD 104 and/or IMD 106, in turn, could be used for external communication devices 108/110.

Figure 2:
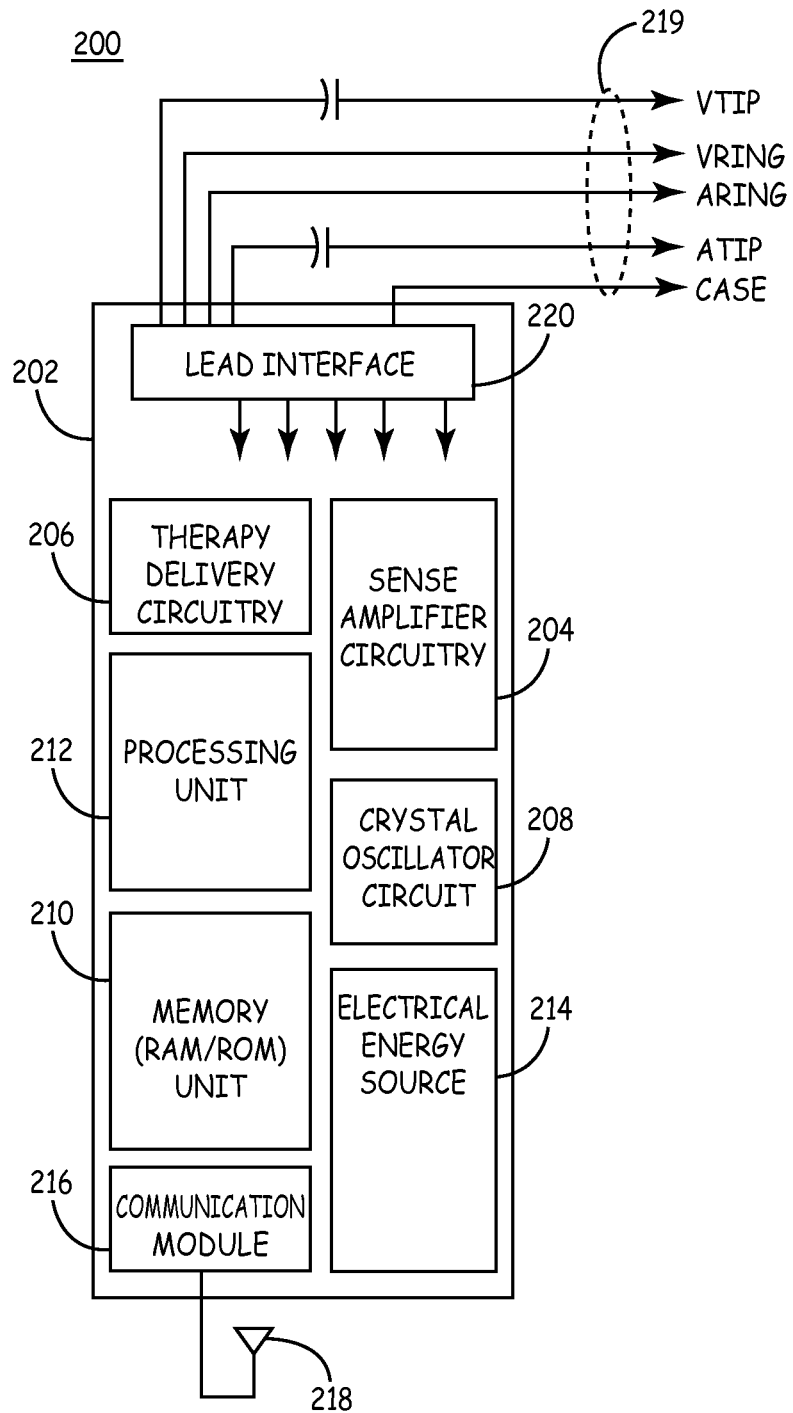
FIG. 2 is a block diagram of example circuitry of an IMD suitable for use in the system depicted in FIG. 1.

FIG. 2 shows an exemplary block diagram of the electronic circuitry of an IMD 200 configured in accordance with certain embodiments of the invention. IMD 104, IMD 106, and/or any other IMD implanted in patient 102 may be configured as shown in FIG. 2. As can be seen from FIG. 2, IMD 200 includes primary circuitry 202 for managing the operation and function of IMD 200, with such primary circuitry 202 being contained within a hermetic enclosure of IMD 200. The primary circuitry 202 includes a number of electrical components, most of which are exemplified in U.S. Pat. No. 6,539,253, entitled "Implantable Medical Device Incorporating Integrated Circuit Notch Filters" (incorporated herein by reference in relevant part). In certain embodiments, the primary circuitry 202 in FIG. 2 includes, without limitation: sense amplifier circuitry 204; therapy delivery circuitry 206; a crystal oscillator circuit 208; a suitable amount of memory 210, which may include random-access memory (RAM) and/or read-only memory (ROM); a processing unit 212; and an electrical energy source 214. In certain embodiments, the primary circuitry 202 also includes a communication module 216 and one or more antennas 219 configured to enable IMD 200 to communicate with other devices within and/or outside the body area network. It should be appreciated that the below descriptions of the primary circuitry 202 within the IMD 200 are merely example configurations.

In certain embodiments, when IMD 200 is used for cardiac applications (e.g., to provide cardiac sensing and pacing functions for the patient), the IMD 200 is coupled to the one or more endocardial leads 219 which, when implanted, extend transvenously between the implant site of the IMD 200 and the patient's heart, as previously noted with reference to FIG. 1. As mentioned above, the physical connections between the leads 219 and the various internal components of IMD 200 are facilitated by means of a conventional connector block assembly. Electrically, the coupling of the conductors of the leads 219 and internal electrical components of IMD 200 may be facilitated by means of a lead interface circuit 220 which functions, in a multiplexer-like manner, to selectively and dynamically establish necessary connections between various conductors in the leads 219 and individual electrical components of the IMD 200, as would be familiar to those of ordinary skill in the art. In certain embodiments, with respect to such cardiac applications, the various conductors in the leads 219 can include atrial tip and ring electrode conductors, $A_{TIP}$ and $A_{RING}$, and ventricular tip and ring electrode conductors, $V_{TIP}$ and $V_{RING}$. For the sake of clarity, the specific connections between the leads 219 and the various components of the IMD 200 are not shown in FIG. 2, although such connections will be familiar to those of ordinary skill in the art. For example, in cardiac applications, the leads 219 will necessarily be coupled, either directly or indirectly, to the sense amplifier circuitry 204 and the therapy delivery circuitry 206, in accordance with common practice, such that cardiac electrical signals may be conveyed to the sense amplifier circuitry 204 and such that stimulating pulses may be delivered by the therapy delivery circuitry 206 to cardiac tissue, via the leads 219. Also not shown in FIG. 2 is the protection circuitry commonly included in implanted devices to protect, for example, the sensing circuitry of the device from high voltage stimulating pulses.

As previously noted, the primary circuitry 202 includes the processing unit 212 which generally varies in sophistication and complexity depending upon the type and functional features of the IMD 200. In certain embodiments, the processing unit 212 can be an off-the-shelf programmable microprocessor, a microcontroller, a custom integrated circuit, or any of a wide variety of other implementations generally known. Although specific connections between the processing unit 212 and other components of the IMD 200 are not shown in FIG. 2, it will be apparent to those of ordinary skill in the art that the processing unit 212 functions to control the timed operation of the sense amplifier circuitry 204 and the therapy delivery circuitry 206. In certain embodiments, the functioning of the processing unit 212 would be under control of firmware and programmed software algorithms stored in memory 210 (e.g., RAM, ROM, PROM and/or reprogrammable ROM) and are carried out using a processing unit of a typical microprocessor core architecture. In certain embodiments, the processing unit 212 can also include a watchdog circuit, a DMA controller, a lock mover/reader, a CRC calculator, and other specific logic circuitry coupled together by on-chip bus, address bus, and power, clock, and control signal lines in paths or trees in a manner well known in the art.

In certain embodiments, as is known in the art, the electrical energy source 214 powers the primary circuitry 202 and can also be used to power electromechanical devices, such as valves or pumps, of a substance delivery IMD, or to provide electrical stimulation energy of an ICD shock generator, cardiac pacing pulse generator, or other electrical stimulation generator. In certain embodiments, the electrical energy source 214 is a high energy density, low voltage battery coupled with a power supply circuit having power-on-reset ("POR") capability. The power supply circuit provides one or more low voltage power supply signals, the POR signal, one or more voltage reference sources, current sources, an elective replacement indicator ("ERI") signal, and, in the case of an ICD, high voltage power to the therapy delivery circuitry 206. For the sake of clarity in the example block diagram provided in FIG. 2, the connections between the electrical energy source 214 and the electrical components of the IMD 200 are not shown, as one skilled in the art would be familiar with such connections.

In certain embodiments, the sense amplifier circuitry 204 can be configured to process physiologic signals that are used to trigger or modulate therapy delivery and are stored as physiologic signal data for later retrieval as described herein. Generally, the sense amplifier circuitry 204 is coupled to electrical signal sense electrodes and/or physiologic sensors on or in the housing of the IMD 200 or as mentioned above, situated at sites distanced from the IMD housing, typically in distal portions of the elongated leads 219. As is generally known, the sensors or electrodes located outside the housing are coupled by conductors to feedthrough pins of feedthroughs extending through the housing wall. Certain physiologic sensors or sense electrodes can be mounted to a connector assembly so that the conductors are quite short.

In certain embodiments, the conductors include the elongated conductors of the leads 219 extending to the remotely situated physiologic sensors and sense electrodes. As such, in some cardiac applications, the sense amplifier circuitry 204 is designed to receive electrical cardiac signals from the leads 219 and to process such signals to derive event signals reflecting the occurrence of specific cardiac electrical events, including atrial contractions (P-waves) and ventricular contractions (R-waves). These event-indicating signals are provided to the processing unit 212 for use in controlling the synchronous stimulating operations of the IMD 200 in accordance with common practice in the art. In addition, these event indicating signals may be communicated, via uplink transmission, to one or more external communication devices.

In example embodiments, the therapy delivery circuitry 206 can be configured to deliver electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart. Alternatively, in certain embodiments, the therapy delivery circuitry 206 can be configured as a drug pump delivering drugs into organs for therapeutic treatment or into the spinal column for pain relief. Alternatively, in certain embodiments, the therapy delivery circuitry 206 can be configured to operate an implantable heart assist device or pump implanted in patients awaiting a heart transplant operation.

When the IMD 200 is used for cardiac applications, the sense amplifier circuitry 204 may also include patient activity sensors or other physiologic sensors for sensing the need for cardiac output and modulating pacing parameters accordingly through many alternative approaches set forth in the prior art. If the IMD 200 is an ICD, the therapy delivery circuitry 206 generally includes one or more high power cardioversion/defibrillation output capacitors, electronic circuitry coupled to the sense amplifiers for detecting and discriminating pathologic and/or nonpathologic arrhythmias from one another and providing other functions, high voltage electronic circuitry for charging the output capacitor(s) from a battery voltage to a higher voltage, and electronic switching circuitry for dumping the charge built up on the output capacitor(s) through the cardioversion/defibrillation electrodes operatively coupled to the one or more endocardial leads 219. Such IMDs are described in detail in U.S. Pat. Nos. 5,626,620 and 5,931,857.

Registers of the memory 210 can be used for storing data compiled from sensed cardiac activity and/or relating to device operating history or sensed physiologic parameters. Generally, the data storage can be triggered manually by the patient, on a periodic basis, or by detection logic (e.g., within the sense amplifier circuitry 204) upon satisfaction of certain programmed-in event detection criteria. If not manually triggered, in certain embodiments, the criteria for triggering data storage within the IMD 200 is programmed via telemetry transmitted instructions and parameter values. If manually triggered, in some cases, the IMD 200 includes a magnetic field sensitive switch (this may be a Hall effect sensor, or another received communications signal) that closes in response to a magnetic field, and the closure causes a magnetic switch circuit to issue a switch closed ("SC") signal to the processing unit 212 which responds in a "magnet mode." For example, the patient may be provided with a magnet (e.g., incorporated into an external communication device) that can be applied over the IMD 200 to close the switch and prompt the processing unit 212 to store physiologic episode data when the patient experiences certain symptoms and/or deliver a therapy to the patient. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

Memory 210 may also be used to store data necessary to support the power adjustment procedures described herein. For example, memory 210 may be configured to store telemetry communication device identifiers, telemetry communication device information, IMD device type information, data type categories, and/or other items that are processed by IMD 200. Memory 210 may also be configured to store power scaling instructions, scaling control signals, or power scaling settings for the transmitter and/or receiver of IMD 200.

In certain embodiments, the crystal oscillator circuit 208 generally employs clocked CMOS digital logic ICs having a clock signal provided by a crystal (e.g., piezoelectric) and a system clock coupled thereto as well as discrete components, e.g., inductors, capacitors, transformers, high voltage protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 200 (e.g., processing unit 212) are omitted from FIG. 2 for the sake of clarity.

Those of ordinary skill in the art will appreciate that IMD 200 may include numerous other components and subsystems, for example, activity sensors and associated circuitry. The presence or absence of such additional components in IMD 200, however, is not believed to be pertinent to the present invention, which relates to the implementation and operation of a communication subsystem in the IMD 200, and associated communication subsystems in one or more of further implantable medical instrumentation and other electrical devices, such as external communication devices.

In certain embodiments, the IMD 200 can involve an implantable cardiac monitor without therapy delivery system 206, e.g., an implantable EGM monitor for recording the cardiac electrogram from electrodes remote from the heart as disclosed in U.S. Pat. No. 5,331,966. Alternatively, the IMD 200 can involve an implantable hemodynamic monitor ("IHM") for recording cardiac electrogram and other physiologic sensor derived signals, e.g., one or more of blood pressure, blood gases, temperature, electrical impedance of the heart and/or chest, and patient activity. The MEDRONIC® REVEAL® insertable loop recorder, having EGM electrodes spaced across its housing, is an example of the former, and the MEDRONIC® CHRONICLE® IHM, coupled with a capacitive pressure and temperature sensing lead and EGM sense electrodes of the type described in U.S. Pat. No. 5,564,434 is an example of the latter.

As described above, the IMD 200 includes communication module 216 and one or more antennas 218. Communication module 216 may include any number of transmitters, any number of receivers, and/or any number of transceivers, depending upon the particular implementation. As described in more detail below, IMD 200 may include power scaling logic, which may be realized in or executed by communication module 216, processing unit 212, memory unit 210, and/or elsewhere in IMD 200. In certain embodiments, each of the antennas 218 is mounted to the IMD 200 in one or more of a wide variety of configurations. For example, one or more of the antennas 218 can take the form of a surface mounted antenna (e.g., as described in U.S. Pat. No. 4,401,119, or one or more of the antennas 218 can be enclosed within or mounted to the IMD connector block assembly. However, it is to be appreciated that the invention should not be limited to such.

It is desirable to reduce the size of the IMD 200 while increasing its functional capabilities and prolonging battery life to increase longevity. In this regard, IMD 200 may be suitably configured to adjust its power characteristics as needed in response to information related to the telemetry communication environment, the context of the telemetry data, or the like. For example, the gain or output power of the transmitter(s) in IMD 200 may be adjusted upwardly or downwardly according to the type of external device that is communicating with IMD 200. In accordance with certain embodiments, the current consumption of certain transceiver circuits can also be increased or decreased to accomplish that goal.

By way of background, the IMD telemetry system and functions are described as follows. For convenience of description, the embodiments described as follows use short range RF downlink telemetry transmissions and uplink telemetry transmissions, but it should be appreciated that the embodiments of the invention should not be limited to such. Similarly, the terms "telemeter," "telemetry transmission," and the like are intended to embrace any such action and manner of communicating and conveying data and commands between the IMD 200 and other electrical devices (e.g., other IMDs implanted within the same patient, external communication devices carried or worn by the patient, and/or external monitoring devices) in the uplink transmission direction and the downlink transmission direction.

In the IMD 200, uplink and downlink telemetry capabilities are provided to enable communication with other devices. IMD 200 may be configured to communicate in a conventional manner with one or more external electrical devices, a telemetry communication device, a more proximal medical device on the patient's body, or other implantable medical instrumentation in the patient's body. Generally, the stored physiologic data as well as one or more of real-time generated physiologic data and non-physiologic data (collectively referred to herein as "patient data") can be transmitted by uplink RF telemetry from the IMD 200 to the other devices or instrumentation in response to a downlink telemetered interrogation command, events within the IMD 200 or the patient, magnet swipe across the IMD 200 by the patient, upon satisfaction of certain programmed-in event detection criteria and/or timed events. The real-time physiologic data can include real time sampled signal levels, e.g., intracardiac electrocardiogram amplitude values, and sensor output signals. The non-physiologic patient data can include currently programmed device operating modes and parameter values, battery condition, device ID, patient ID, implantation dates, device programming history, real time event markers, and the like. In the context of implantable pacemakers and ICDs, such patient data can include programmed sense amplifier sensitivity, pacing or cardioversion pulse amplitude, energy, and pulse width, pacing or cardioversion lead impedance, programmed setting, and/or accumulated statistics related to device performance, e.g., data related to detected arrhythmia episodes and applied therapies.

Figure 3:
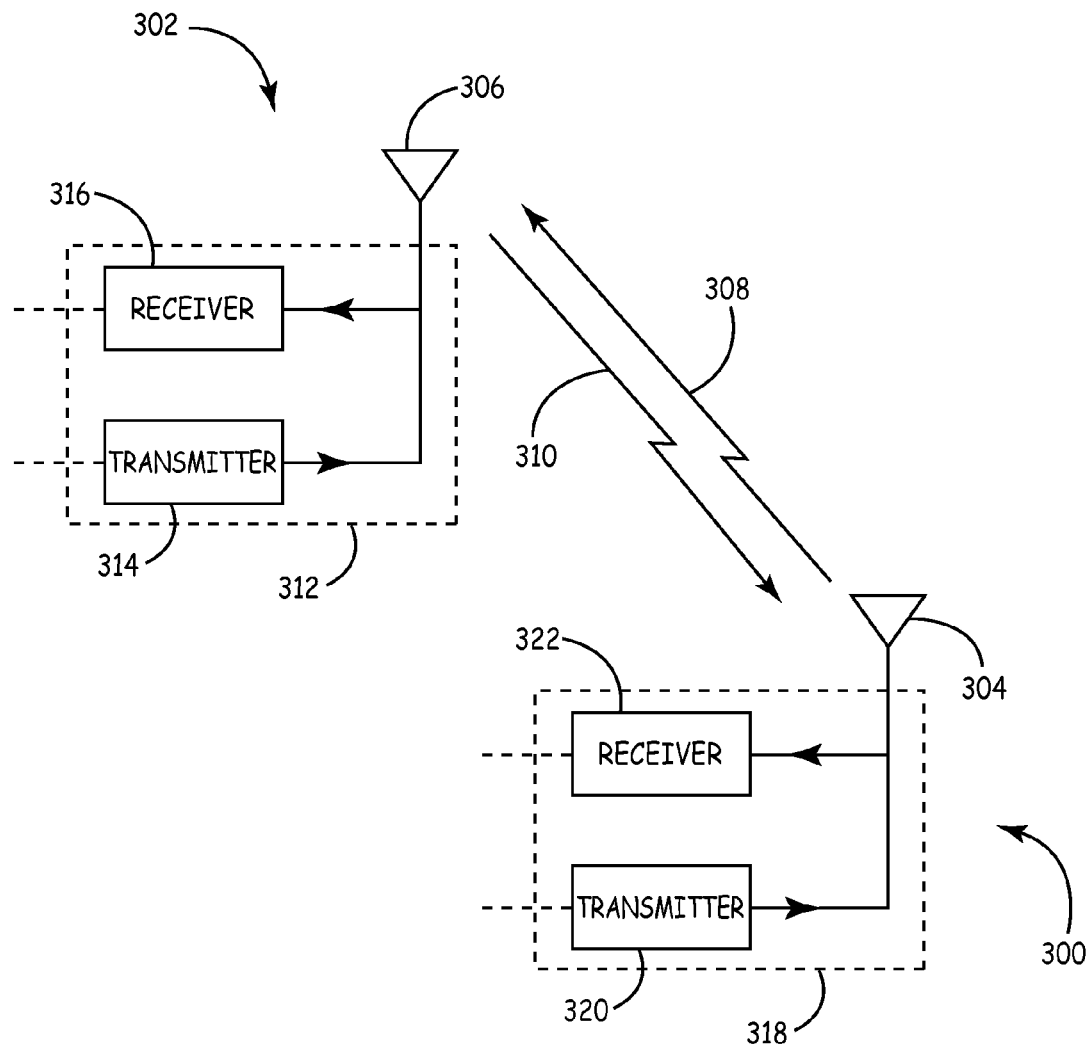
FIG. 3 is a block diagram depicting example communication modules suitable for use in an IMD communication system.

FIG. 3 depicts data communication between an IMD 300 and another device 302, which may be a device within the same body area network or any telemetry communication device. In certain embodiments, programming commands or patient data can be transmitted between one or more IMD antennas 304 associated with the IMD 300 and one or more antennas 306 associated with the device 302. In certain embodiments, a high frequency signal (or UHF, or VHF signal) can be employed. As such, it would not be necessary for antenna 306 to be held in close proximity to IMD 300. In other words, the system shown in FIG. 3 may be configured to support far field telemetry. For example, an external communication device 302 and an external communication device antenna 306 may be on a stand a few meters or so away from the patient. Moreover, the patient may be active and could be exercising on a treadmill or the like during a telemetry interrogation and transmission of real time ECG or physiologic parameters. An external communication device 302 may also be designed to universally program existing IMDs that employ the conventional ferrite core, wire coil, RF telemetry antenna of the prior art and therefore also have a conventional external communication device RF head and associated software for selective use with such IMDs.

In an uplink telemetry transmission 308, the antenna 306 operates as a telemetry receiver antenna, and the antenna 304 operates as a telemetry transmitter antenna. Conversely, in a downlink telemetry transmission 310, the antenna 306 operates as a telemetry transmitter antenna, and the antenna 304 operates as a telemetry receiver antenna. As shown with respect to FIG. 1, such telemetry transmissions may also be supported between two IMDs implanted within the same patient.

In certain embodiments, antenna 306 is electrically coupled to a telemetry transceiver or radio 312, which may include a telemetry transmitter 314 and a telemetry receiver 316. Similarly, in certain embodiments, antenna 304 is coupled to a telemetry transceiver or radio 318, which may include a telemetry transmitter 320 and a telemetry receiver 322. Referring to FIG. 2, telemetry transceiver 318 may be included within communications module 216 of the IMD 200. Alternatively, telemetry transceiver 318 may be coupled to communications module 216 to enable IMD operation as described herein. In certain embodiments, the telemetry transmitter and telemetry receiver of a given device can be coupled to control circuitry and registers under the control of a microcomputer and software maintained by the device.

In practice, the telemetered data can be encoded in any of a wide variety of telemetry formats. While not being limited to such, some examples of particular data encoding or modulation types and/or techniques that can be utilized with such data transmissions include noise modulation, general spread spectrum encoding, bi-phase encoding, quadrature phase shift keying, frequency shift keying ("FSK"), time division multiple access ("TDMA"), frequency division multiple access ("FDMA"), pre-emphasis/de-emphasis of baseband, vestigial, code division multiple access ("CDMA"), quadrature amplitude modulation ("QAM"), pi/8, quad-QAM, 256-QAM, 16-QAM, delta modulation, phase shift keying ("PSK"), quadrature phase shift keying ("QPSK"), quadrature amplitude shift keying ("QASK"), minimum shift keying, tamed frequency modulation ("TFM"), orthogonal frequency division multiplexing ("OFDM"), Bluetooth, any 802.11 modulation configuration, worldwide interoperability for microwave access ("WiMAX"), any 802.16 modulation configuration, 802.15.4, and Zigbee. Note that the "mode" used by the transceivers may be selected to optimize performance based on implant depth input and QoS input.

In certain embodiments, the uplink and downlink telemetry transmissions 308/310 between the IMD 300 and the device 302 follow a telemetry protocol that formulates, transmits, and demodulates data packets each comprising a bit stream of modulated data bits. In certain embodiments, the data packets are formulated of a data bit stream with a preamble, data and error checking data bits.

Figure 4:
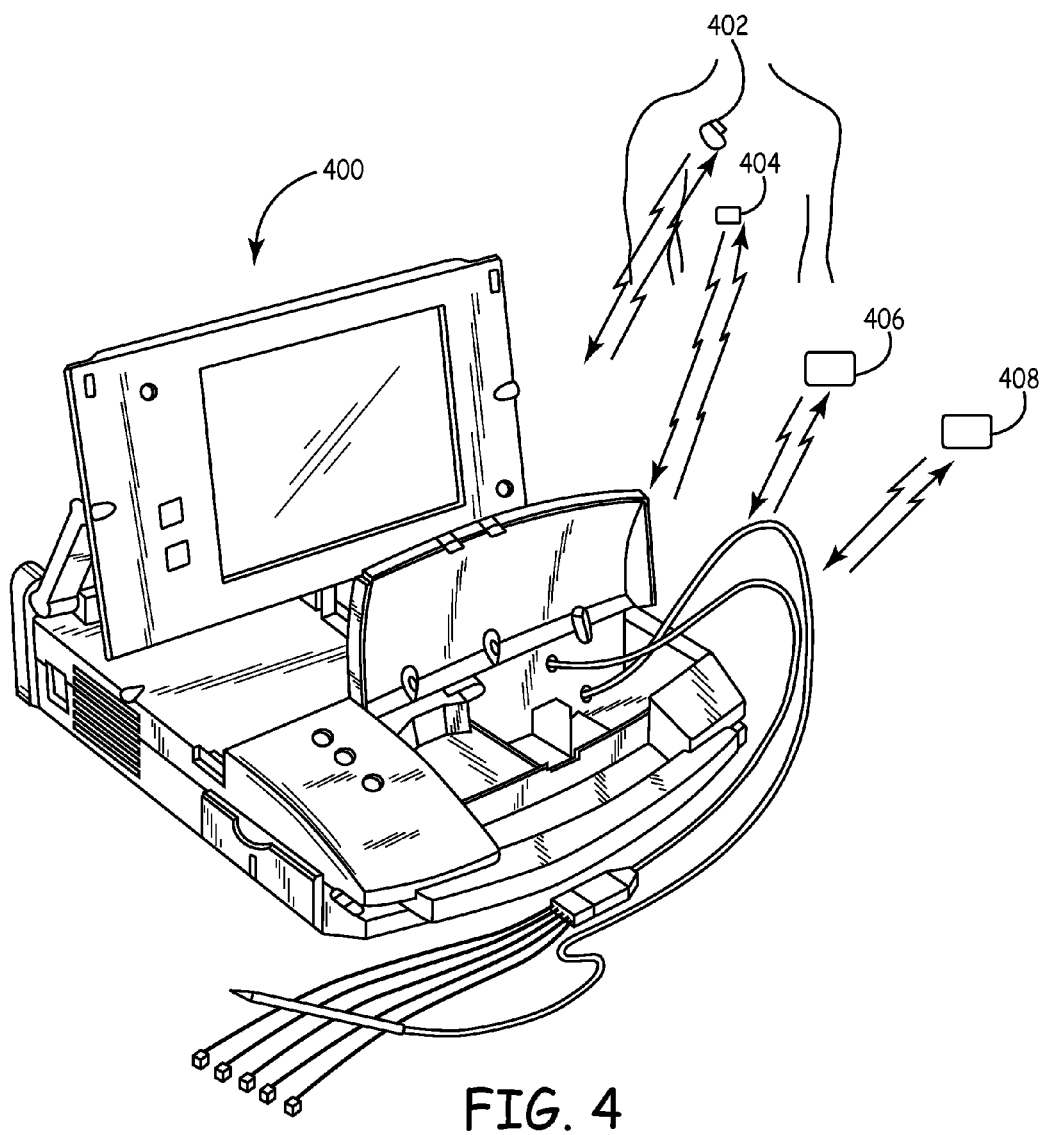
FIG. 4 is a perspective view of an external telemetry communication device configured to communicate with an IMD in accordance with certain embodiments of the invention.

In FIG. 4, there is shown a perspective view of an external device 400 configured in accordance with certain embodiments of the invention. In certain embodiments, the external device 400 can be used for telemetry communication with any number of IMDs 402/404 and/or any number of external communication devices 406/408. From such telemetry communications, the external device 400 can be subsequently used to display or further transmit patient data. The external device 400 generally includes a processing unit (not visibly shown). As should be appreciated, the processing unit can include any of a wide variety of devices. While not being limited to such, the processing unit, in certain embodiments, can be a personal computer type motherboard, e.g., a computer motherboard including a microprocessor and related circuitry such as digital memory. The details of design and operation of the computer system will not be set forth in detail in the present disclosure, as it is believed that such details are well-known to those of ordinary skill in the art. However, such external processing monitors are described in more detail in U.S. Pat. Nos. 5,345,362 and 5,683,432, which are incorporated herein by reference in their relevant parts. While not shown, it is to be appreciated that such telemetry communications between the external device 400 and the devices within the body area network (e.g., IMDs 402/404 and external communication devices 406/408) can occur in combination with telemetry communications occurring between IMDs 402/404, between external communication devices 406/408, and/or between one or more of the IMDs 402/404 and one or more of the external communication devices 406/408 (as exemplified in FIG. 1).

As described in more detail below, external device 400 may be suitably configured to function as an IMD programming device that provides data, programming instructions, and other information to an example IMD that supports power scaling. Moreover, external device 400 may be a telemetry communication device that provides a device identifier to the IMD, where the IMD can process the device identifier to determine how best to adjust the IMD power characteristics to suit the needs and demands of external device 400. This feature is desirable when the IMD is configured to support telemetry communications with multiple external devices. Moreover, a telemetry communication channel may be maintained between an IMD and external device 400 to provide quality of service information to the IMD for use during power scaling.

Figure 5:
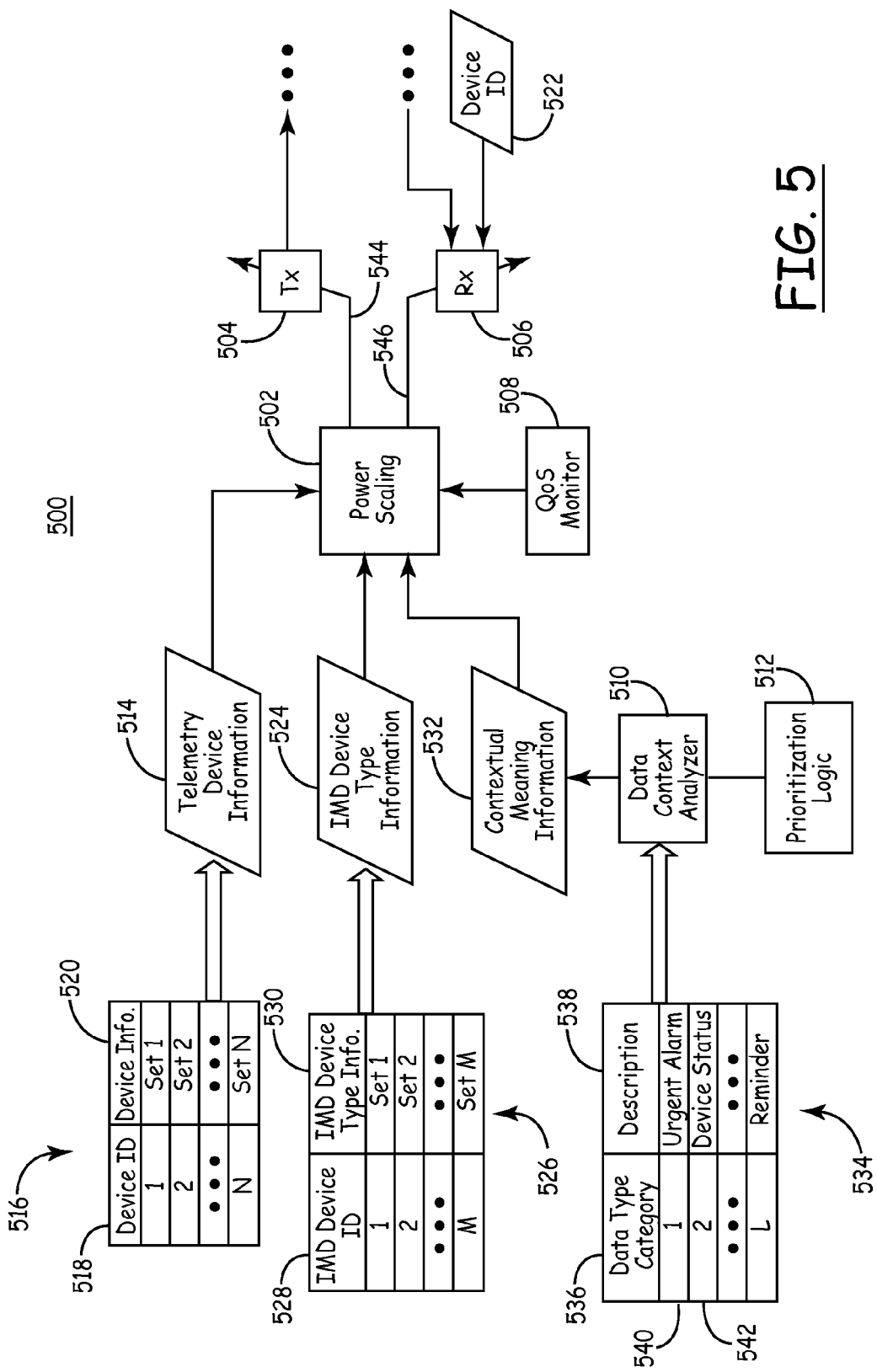
FIG. 5 is a schematic representation of a portion of an example IMD that supports power scaling in accordance with example embodiments of the invention.

FIG. 5 is a schematic representation of a portion of an example IMD 500 that supports power scaling based upon different criteria as explained below. IMD 500 is one example of an IMD that supports the various power adjustment techniques described herein. It should be appreciated that FIG. 5 is a very simplified depiction of a portion of IMD 500, and that an embodiment of IMD 500 will include additional components and logic that support conventional operating aspects of IMD 500. For example, an embodiment of IMD 500 may include the components and logic described above with respect to FIG. 2. It should also be appreciated that an embodiment of an IMD need not support all of the power scaling modes and features described herein, however, IMD 500 is depicted as a "full featured" version for convenience. IMD 500 may include power scaling logic 502, at least one transmitter 504, at least one receiver 506, a quality of service ("QoS") monitor 508, a data context analyzer 510, and prioritization logic 512. In practice, transmitter 504 and receiver 506 may be realized in one transceiver or radio module. IMD 500 also includes an appropriate amount of memory for storing data processed by IMD 500 in the context of the power scaling routines described herein. These components and logic may be coupled as needed using any suitable interconnection architecture.

Depending upon the particular implementation, power scaling logic 502 may be configured to process telemetry device information 514 in the manner described below. Telemetry device information 514 is information pertaining to a telemetry communication device for IMD 500. In this regard, telemetry device information 514 is indicative of characteristics of the telemetry communication device that might influence power adjustments of IMD 500. For example, telemetry device information 514 may be indicative of the device type for the particular telemetry communication device, e.g., whether the telemetry device is an external programming device, a monitor device for IMD 500, a controller device for IMD 500, a computer device, a physiologic characteristic sensor for the patient, a display device, or the like. In practice, the telemetry device type may influence the power adjustment of IMD 500—some telemetry communication devices (such as a sensor worn by or attached to the patient) will always be located within a short range of IMD 500, while other telemetry communication devices (such as a far field programmer or a long range monitor device) need not be so constrained. Consequently, IMD 500 can reduce its transmit power for short range telemetry devices and increase its transmit power for far field telemetry devices. As another example, telemetry device information 514 may be indicative of a priority for telemetry communications between IMD 500 and the given telemetry communication device, where certain telemetry devices can be treated as priority devices relative to other telemetry devices. IMD 500 can therefore increase its transmit power for such priority telemetry devices. A monitor for IMD 500 may, for example, be treated as a priority telemetry device relative to other telemetry devices. Other priority communications may be, for example, communication from a sensor to IMD 500, and communication from IMD 500 to a drug pump. As yet another example, telemetry device information 514 may be indicative of a desired or default telemetry range for the telemetry communication device. In this regard, telemetry device information 514 may convey a minimum, maximum, typical, average, or other distance measurement (in inches, centimeters, feet, meters, etc.) for telemetry communications with the given telemetry communication device. Such a distance measurement can be processed by IMD 500 to ensure that it does not waste energy by transmitting signals at an unnecessarily high power.

Power scaling logic 502 may receive telemetry device information 514 in any appropriate manner. For example, power scaling logic 502 may receive telemetry device information 514 from memory 516 of IMD 500. Referring again to FIG. 2, memory 516 may be realized in memory unit 210. Memory 516, which is coupled to power scaling logic 502, may be configured to store a list of device identifiers 518 for a number of telemetry communication devices that are compatible with IMD 500. The ellipses in memory 516 indicate that memory 516 can store any number (N) of device identifiers 518 along with their respective sets of telemetry device information 520. In this example, each device identifier 518 has corresponding telemetry device information 520 for the respective telemetry communication device. In the example embodiment, IMD 500 is suitably configured to receive (via receiver 506) a device identifier 522 from the telemetry communication device. This device identifier 522 is then utilized to access the corresponding telemetry device information 514 from memory 516.

FIG. 5 depicts one example environment where telemetry device information 514 is stored and obtained locally at IMD 500. Although not specifically shown in FIG. 5, receiver 506 may receive telemetry device information 514 in a telemetry communication from an IMD programming device such that IMD 500 can process telemetry device information 514 in an appropriate manner and provide telemetry device information 514 to power scaling logic 502. In alternate embodiments, IMD 500 may be configured to receive telemetry device information 514 from the telemetry communication device itself, from another external source, any telemetry communication device, via manipulation of a user interface of IMD 500, via a wireless and/or wired connection to a computing device (e.g., a personal computer, a laptop computer, a personal digital assistant, etc.), from a portable data storage device, or the like.

Depending upon the particular implementation, power scaling logic 502 may be configured to process IMD device type information 524 in the manner described below. IMD device type information 524 is information that is indicative of the current telemetry communication context for IMD 500. In this regard, the current telemetry communication context may represent a configuration type for IMD 500, where the configuration type might influence power adjustments of IMD 500. For example, IMD device type information 524 may be indicative of the device type for IMD 500, e.g., whether IMD 500 is a defibrillator device, a pacemaker device, a drug delivery device, a physiologic characteristic sensor, or the like. The configuration type for IMD 500 may be utilized to program a generic IMD radio or communication module to suit the needs of the particular application. In this manner the configuration type may influence the power adjustment of IMD 500—some IMDs (such as a sensor worn by or attached to the patient) will always transmit short range telemetry communications, while other IMDs need not be so constrained. Other examples of short range telemetry communications include, without limitation: communication between a pacemaker and an ICD; communication between a drug pump and an ICD; communication between multiple sensors and a drug pump; communication between two drug pumps; and communication between IMD 500 and a device worn by the patient. Consequently, IMD 500 can reduce its transmit power to accommodate short range telemetry communications and increase its transmit power to accommodate far field telemetry communications. As another example, the current telemetry communication context may represent or indicate a priority for telemetry communications between IMD 500 and the given telemetry communication device, where certain telemetry communications can be treated as priority communications relative to other telemetry communications. IMD 500 can therefore increase its transmit power for such priority telemetry communications. Communications with a monitor for IMD 500 may, for example, be treated as priority telemetry communications relative to communications with other devices. Additional examples of external device types that may be treated with higher priority include, without limitation: patient-worn devices; a home patient monitor; a transponder; or a physician programmer. As yet another example, the current telemetry communication context may represent or indicate a desired or default telemetry range for the IMD. In this regard, IMD device type information 524 may convey a minimum, maximum, typical, average, or other distance measurement (in inches, centimeters, feet, meters, etc.) for telemetry communications with expected telemetry communication devices. Such distance measurements may be suitable for use with IMDs that only communicate with one or a small number of known external devices. In the example embodiment, such a distance measurement can be processed by IMD 500 to ensure that it does not waste energy by transmitting signals at an unnecessarily high power. As another example, the current telemetry communication context may represent or indicate a current application mode for IMD 500. In this context, an "application mode" is a functional mode of operation for IMD 500. For example a given IMD may be configured to support a plurality of operating modes, a plurality of telemetry features, or the like. The current application mode for IMD 500 represents its operating state at that moment in time. Consequently, IMD device type information 524 may also convey information about the functional state of IMD 500, and that functional state may influence or otherwise impact the power characteristics of IMD 500 as described herein.

Power scaling logic 502 may receive IMD device type information 524 in any appropriate manner. For example, power scaling logic 502 may receive IMD device type information 524 from memory 526 of IMD 500. Referring again to FIG. 2, memory 526 may be realized in memory unit 210. Memory 526, which is coupled to power scaling logic 502, may be configured to store a list of IMD device identifiers 528 that represent the current operating state, functional mode, and/or configuration type for IMD 500. The ellipses in memory 526 indicate that memory 526 can store any number (M) of IMD device identifiers 528 along with their respective sets of IMD device type information 530. In this example, each IMD device identifier 528 has corresponding IMD device type information 530 for IMD 500. Memory 526 may enable IMD 500 to reconfigure itself as needed to support different operating modes using a single software configurable radio or communication module.

FIG. 5 depicts one example environment where IMD device type information 524 is stored and obtained locally at IMD 500. Although not specifically shown in FIG. 5, receiver 506 may receive IMD device type information 524 in a telemetry communication from an IMD programming device such that IMD 500 can process IMD device type information 524 in an appropriate manner and provide IMD device type information 524 to power scaling logic 502. In alternate embodiments, IMD 500 may be configured to receive IMD device type information 524 from a telemetry communication device, from another external source, via manipulation of a user interface of IMD 500, via a wireless and/or wired connection to a computing device (e.g., a personal computer, a laptop computer, a personal digital assistant, etc.), from a portable data storage device, or the like.

Depending upon the particular implementation, power scaling logic 502 may be configured to process contextual meaning information 532 in the manner described below. Contextual meaning information 532 is information that is indicative of the type, purpose, or function of the data to be transmitted by IMD 500. In this example embodiment, IMD 500 may utilize data context analyzer 510 (or any equivalent processing logic) that determines, processes, or analyzes the context or meaning of the data to be transmitted by IMD 500. Data context analyzer 510 may be suitably configured to consider any number of factors that may influence contextual meaning information 532 and, in turn, influence the power characteristics of IMD 500. For example, data context analyzer 510 may analyze signaling or overhead data contained in a data packet to be transmitted by IMD 500, where such signaling or overhead data identifies the type, operation, function, or purpose of the telemetry data contained in that packet.

In example embodiments, the contextual meaning information 532 may include, represent, or indicate a priority for the data to be transmitted, such that relatively high priority data can be transmitted using higher transmit power and relatively low priority data can be transmitted using lower transmit power. IMD 500 may utilize prioritization logic 512 (or any equivalent processing logic), which can be configured to generate a priority for the data to be transmitted. Prioritization logic 512 may be designed to analyze signaling or overhead data contained in a data packet to be transmitted by IMD 500, where such signaling or overhead data identifies the type, operation, function, or purpose of the telemetry data contained in that packet. In turn, prioritization logic 512 may generate the priority for the data using any suitable procedure (e.g., a table lookup, an appropriate algorithm, or the like). As depicted in FIG. 5, the priority may be processed by data context analyzer 510 such that contextual meaning information 532 is based at least in part upon the priority.

In example embodiments, the contextual meaning information 532 may include, represent, or indicate a data type category for the data to be transmitted. One data type category may correspond to a first IMD power characteristic, while another data type category may correspond to a second IMD power characteristic. For example, a first data type category may correspond to telemetry data that ought to be transmitted at a relatively high transmit power, a second data type category may correspond to telemetry data that ought to be transmitted at a relatively low transmit power, and a third data type category may correspond to telemetry data that ought to be transmitted only once regardless of transmission success. As depicted in FIG. 5, data context analyzer 510 may process the data type category such that contextual meaning information 532 is based at least in part upon the data type category.

Power scaling logic 502 may receive the data type category information in any appropriate manner. For example, IMD 500 may utilize memory 534 to store data type category information. Referring again to FIG. 2, memory 534 may be realized in memory unit 210. Memory 534, which is coupled to power scaling logic 502, may be configured to store a list of data type categories 536 that identify the different categories of data handled by IMD 500. The ellipses in memory 534 indicate that memory 534 can store any number (L) of data type categories 536. Memory 534 may also store descriptions 538 of the specific data or information that falls within the respective data type categories 536. In this example, a first data type category 540 includes urgent alarms; data type category 540 may also include other relatively urgent data items that are treated in a particular manner by IMD 500. In this example, a second data type category 542 includes device status information; data type category 542 may also include other relatively routine data items that are treated in a different manner by IMD 500. In practice, IMD 500 may increase its output transmit power for data type category 540, and decrease its output transmit power for data type category 542.

FIG. 5 depicts one example environment where contextual meaning information 532 is obtained locally at IMD 500, and where the data type category information is stored and obtained locally at IMD 500. Although not specifically shown in FIG. 5, receiver 506 may receive some contextual meaning information 532 and/or some data type category information in telemetry communications from an IMD programming device such that IMD 500 can process the received information in an appropriate manner and provide contextual meaning information 532 to power scaling logic 502. In alternate embodiments, IMD 500 may be configured to receive such information from a telemetry communication device, from another external source, via manipulation of a user interface of IMD 500, via a wireless and/or wired connection to a computing device (e.g., a personal computer, a laptop computer, a personal digital assistant, etc.), from a portable data storage device, or the like.

In the example embodiment, IMD 500 is able to process telemetry device information 514, IMD device type information 524, and/or contextual meaning information 532 in a substantially real-time manner to provide dynamic adjustment of the IMD power characteristics. Thus, IMD 500 can dynamically adjust its operating parameters to conserve energy and extend battery life while maintaining telemetry communication links as needed for the current operating environment, the context of the telemetry data, and the like.

Power scaling logic 502 is suitably configured to generate scaling instructions or scaling control signals in response to telemetry device information 514, IMD device type information 524, and/or contextual meaning information 532. Referring to FIG. 2, in example embodiments, power scaling logic 502 (or portions thereof) can be realized in processing unit 212, memory unit 210, and/or communication module 216. Power scaling logic 502 may include, access, or perform a power scaling algorithm, which may be realized as computer-executable program instructions. In this example, power scaling logic 502 obtains telemetry device information 514, IMD device type information 524, and/or contextual meaning information 532, and generates appropriate scaling instructions for transmitter 504 and/or for receiver 506, where such scaling instructions modify, adjust, or influence the operation of transmitter 504 and/or receiver 506. More specifically, the scaling instructions adjust variable power characteristics of transmitter 504 and/or variable power characteristics of receiver 506 in a manner that can increase battery life of IMD 500 by reducing the overall power consumption of IMD 500.

Transmitter 504 is coupled to power scaling logic 502. Transmitter 504 is configured to transmit telemetry signals from IMD 500, where such telemetry signals may be intended for any suitable device, system, or architecture (e.g., another IMD, an external programming device, a computing device, a telemetry communication device, a monitor, etc.). Transmitter 504 and IMD 500 may leverage known technologies to support telemetry communication according to accepted data transmission protocols, regulations, standards, or the like. In this embodiment, transmitter 504 is suitably configured with variable power characteristics, and is suitably configured to respond to the scaling instructions such that the scaling instructions adjust the variable power characteristics of transmitter 504. In this regard, FIG. 5 depicts a transmitter scaling control signal 544 with an arrowhead that represents adjustment of transmitter 504. The variable power characteristics of transmitter 504 may include, without limitation: the output power of transmitter 504; the gain of one or more amplifier stages in transmitter 504; and a supply voltage utilized by transmitter 504.

Receiver 506 is also coupled to power scaling logic 502. Receiver 506 is configured to receive telemetry signals intended for IMD 500, where such telemetry signals may originate at any suitable device, system, or architecture (e.g., another IMD, an external programming device, a computing device, a telemetry communication device, a monitor, etc.). Receiver 506 and IMD 500 may leverage known technologies to support telemetry communication according to accepted data transmission protocols, regulations, standards, or the like. In this embodiment, receiver 506 is suitably configured with variable power characteristics, and is suitably configured to respond to the scaling instructions such that the scaling instructions adjust the variable power characteristics of receiver 506. In this regard, FIG. 5 depicts a receiver scaling control signal 546 with an arrowhead that represents adjustment of receiver 506. The variable power characteristics of receiver 506 may include, without limitation: the gain of one or more front end components in receiver 506 (such as a low noise amplifier or a mixer); a supply voltage utilized by receiver 506; or the bias current for the receiver. Either or all of the receiver low noise amplifier, mixer, intermediate frequency amplifiers, or channel filters, may have their gains, voltage, current bias, and/or dynamic range adjusted per the implant and QoS parameters. In example embodiments, adjustment of receiver 506 may also be influenced by dynamic range requirements of receiver 506.

IMD 500 may also include QoS monitor 508, which is coupled to power scaling logic 502 in this example. QoS monitor 508 is suitably configured to process at least one QoS parameter for a communication channel between IMD 500 and a telemetry communication device (not shown in FIG. 5). In practice, if QoS monitor 508 determines that the QoS parameter satisfies minimum requirements, then power scaling logic 502 can finalize the power characteristics of IMD 500. In other words, power scaling logic 502 can fix the current adjustments corresponding to transmitter 504 and/or receiver 506. On the other hand, if QoS monitor 508 determines that the QoS parameter is insufficient or inadequate, then power scaling logic 502 may be prompted to perform additional power scaling for transmitter 504 and/or receiver 506.

QoS monitor 508 may generate or determine the QoS parameter(s), or it may only analyze QoS parameter(s) that IMD 500 receives from another device. In this regard, a QoS parameter may be, include, or indicate, without limitation: a link margin value; a signal-to-noise ratio; a received signal strength indicator; a bit error rate or other error indicator; or a measurement of spatial diversity antenna switching for IMD 500 (more switching indicates a weaker telemetry signal).

In alternate embodiments, some or all of the power scaling processing intelligence may reside at an IMD programming device or any telemetry communication device that can link to IMD 500. For example, an IMD programming device may include the power scaling logic and the QoS monitor elements described above. In such an embodiment, the IMD programming device may receive the telemetry device information 514, IMD device type information 524, and/or contextual meaning information 532, perform the power scaling routine, and generate the scaling instructions as generally described above for IMD 500. The IMD programming device, however, could then transfer the scaling instructions (and possibly other information) to the IMD. Thereafter, the IMD can simply execute the scaling instructions, forward the scaling instructions to its transmitter and/or receiver, generate usable scaling control signals from the received scaling instructions, or the like.

Figure 6:
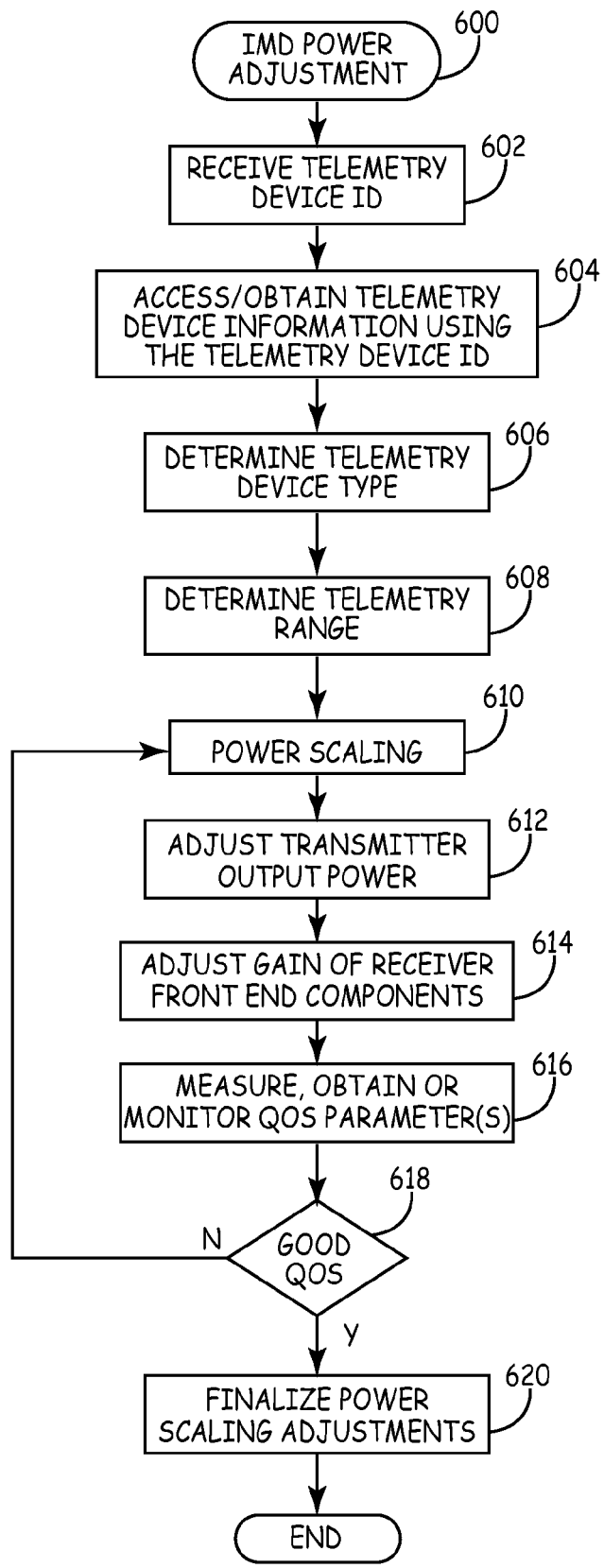
FIGS. 6-8 are flow charts of IMD power adjustment processes according to example embodiments of the invention.
Figure 7:
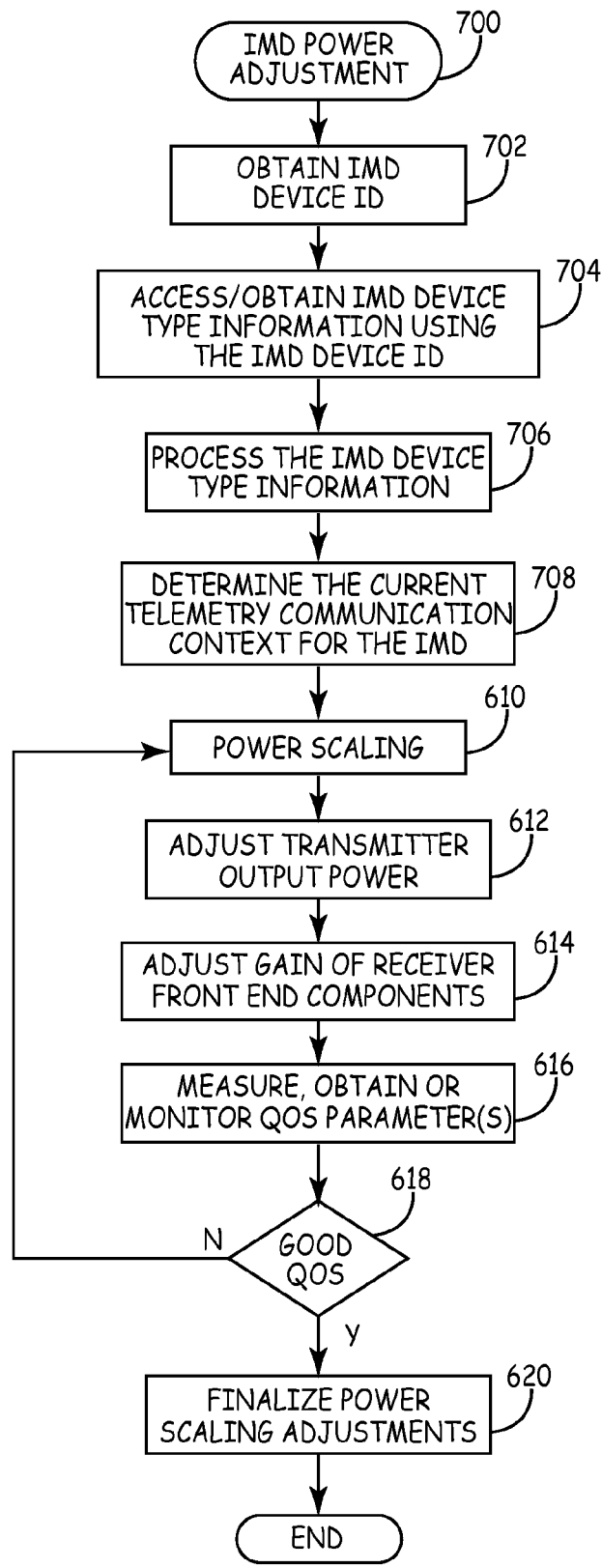
Figure 8:
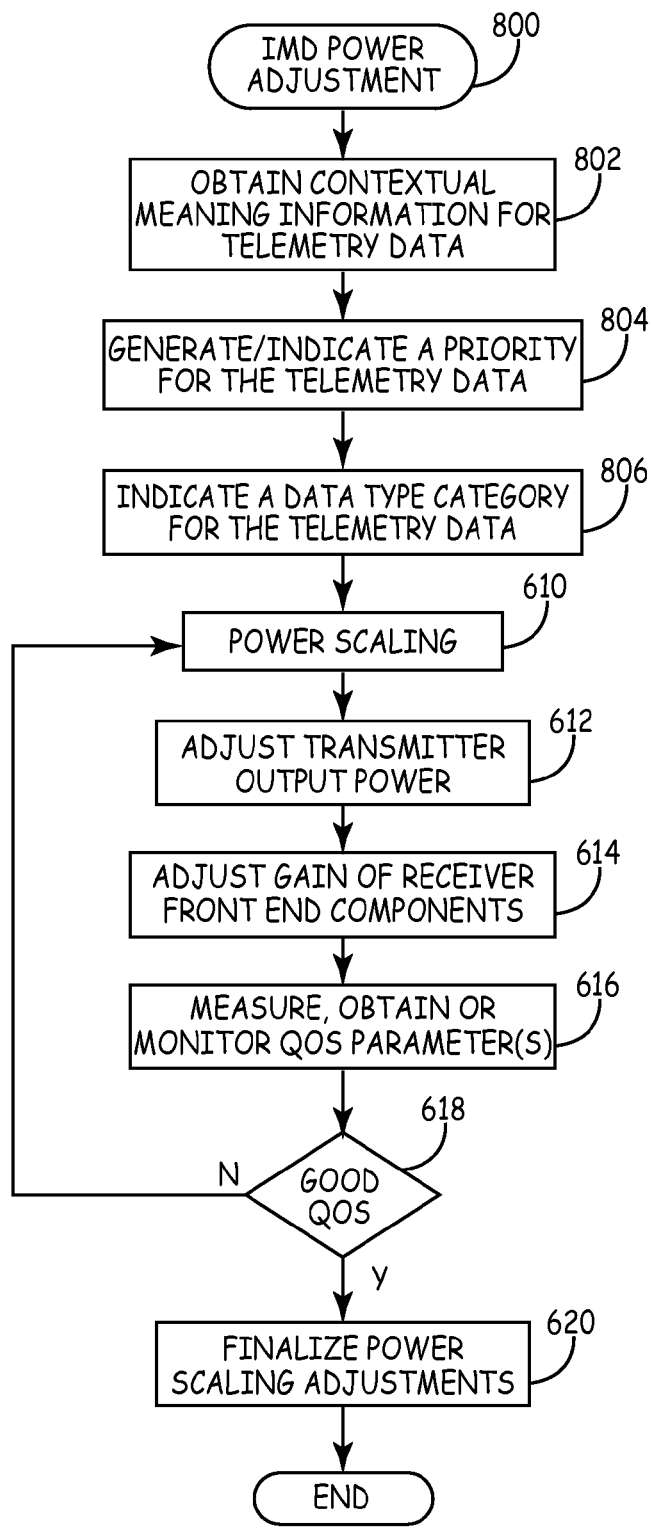

FIGS. 6-8 are flow charts of IMD power adjustment processes according to example embodiments of the invention. The various tasks performed in connection with these processes may be performed by software, hardware, firmware, or any combination thereof. For illustrative purposes, the following description of these processes may refer to elements mentioned above in connection with FIGS. 1-5. In embodiments of the invention, portions of each process may be performed by different elements of the described system, e.g., power scaling logic 502, receiver 506, data context analyzer 510, or QoS monitor 508. Although each process considers an embodiment where the tasks are performed by an IMD, equivalent processes can be executed where at least some of the tasks are performed by an IMD programming device. It should be appreciated that each process may include any number of additional or alternative tasks, the tasks shown in FIGS. 6-8 need not be performed in the illustrated order, and each process may be incorporated into a more comprehensive procedure or process having additional functionality not described in detail herein.

IMD power adjustment process 600 may begin by receiving (task 602) a device identifier for a telemetry communication device, where the telemetry communication device is communicating with the IMD or will be communicating with the IMD. In this example, the IMD receives the telemetry device identifier from the telemetry communication device itself, via an established telemetry link between the IMD and the telemetry communication device. Task 602 may, for example, be performed during initialization of the telemetry session or prior to the telemetry session. Task 602 may also be performed periodically during the telemetry session.

The IMD may process the received telemetry device identifier in an appropriate manner as described above to access or obtain (task 604) information pertaining to the telemetry communication device. In one embodiment, the IMD maintains a list of telemetry device identifiers for a number of telemetry communication devices that are compatible with the IMD, and uses the received telemetry device identifier to perform a table lookup to access the desired information about the telemetry communication device. In practice, the telemetry device information may include, represent, or identify a device type for the telemetry communication device, an assigned priority for the telemetry communication device, a telemetry range for the telemetry communication device, and/or other operating parameters or features associated with the telemetry communication device. The device type may be indicative of other parameters, features, or characteristics of the telemetry communication device. For example, the device type may be indicative of the priority for telemetry communications between the IMD and the telemetry communication device. In this regard, process 600 may determine (task 606), from the telemetry device information, a device type for the telemetry communication device, and/or determine (task 608), from the telemetry device information, a telemetry range for the telemetry communication device. Such determinations may be accomplished using any suitable processing logic or procedure.

In response to the telemetry device information obtained during task 604, IMD power adjustment process 600 may perform a suitable power scaling routine for the IMD (task 610). In this example, the power scaling routine is based upon the telemetry device information. Alternatively or additionally, the power scaling routine may be based upon IMD device type information and/or contextual meaning information (as described herein). For process 600, the power scaling logic of the IMD performs this power scaling routine to generate scaling instructions or control signals in response to the telemetry device information. The scaling instructions may be appropriately formatted for interpretation by the IMD transmitter, the IMD receiver, and/or the IMD transceiver, depending upon the particular implementation. For example, if the telemetry device information identifies the telemetry communication device as a device that is attached to the patient's body, then the transmitter output power and receiver front end gain may be scaled down by a relatively large amount. If, however, the telemetry device information identifies the telemetry communication device as a far field programmer device for the IMD, then the transmitter output power and receiver front end gain may not be scaled down at all.

The power scaling routine influences the adjustment of one or more power characteristics of the IMD. For example, the scaling instructions may initiate, cause, or control the adjusting of transmitter output power for the IMD (task 612), the adjusting of the gain of one or more receiver front end components for the IMD (task 614), and/or the adjusting of any parameter, quantity, feature, setting, circuit, or component of the IMD that might otherwise influence the power consumption of the IMD, including, without limitation, any of the specific items listed in the description of transmitter 504 and receiver 506 (see FIG. 5).

In this example embodiment, IMD power adjustment process 600 measures, obtains, or monitors at least one QoS parameter for a communication channel between the IMD and a telemetry communication device (task 616). During task 616, the IMD or the telemetry communication device processes the at least one QoS parameter to determine whether the at least one QoS parameter satisfies minimum requirements. In this regard, process 600 may perform a query task 618 to check whether the at least one QoS parameter is "good" for the particular application and operating environment, as mentioned above in the context of QoS monitor 508 (see FIG. 5). If the at least one QoS parameter meets the minimum requirements, i.e., if the QoS for the measured channel is acceptable, then process 600 may finalize the power characteristics of the IMD by fixing the current power scaling adjustments (task 620). On the other hand, if the QoS for the measured channel does not meet the minimum requirements, then process 600 may be re-entered at task 610. Thus, if the current power characteristics settings do not result in an acceptable QoS, then process 600 can repeat the power scaling routine to generate new power scaling instructions for the IMD. This subsequent iteration of the power scaling routine may process the at least one QoS parameter and/or data that is indicative of the level of satisfaction determined during query task 618. This additional information may be desirable to enable the power scaling routine to intelligently generate new scaling instructions to further adjust the IMD transmitter, the IMD receiver, and/or the IMD transceiver in an appropriate manner.

IMD power adjustment process 700 may begin by obtaining (task 702) an IMD device type identifier for the IMD. In example embodiments, the IMD itself may provide the IMD device type identifier, the IMD may receive the IMD device type identifier from another device, or the IMD may receive the IMD device type identifier during a setup or initialization procedure for the IMD. Task 702 may be desirable for IMD implementations that might utilize a "generic" radio or communication module, where the generic module can be suitably configured for operation in an appropriate manner after manufacturing. Task 702 may, for example, be performed during initialization of the telemetry session or prior to the telemetry session. Task 702 may also be performed periodically during the telemetry session.

The IMD may process the received IMD device type identifier in an appropriate manner as described above to access or obtain (task 704) IMD device type information that is indicative of a current telemetry communication context for the IMD. In one embodiment, the IMD maintains a list of IMD device type identifiers, and uses the received IMD device type identifier to perform a table lookup to access the desired IMD device type information. In practice, the IMD device type information (or the current telemetry communication context) may include, represent, or identify a configuration type for the IMD, a priority for telemetry communications between the IMD and a telemetry communication device, a telemetry range for the IMD or for a telemetry communication device, a current application mode for the IMD, and/or other operating parameters or features associated with the IMD. In this regard, process 700 may process (task 706) the IMD device type information in an appropriate manner to determine (task 708) the current telemetry communication context for the IMD. The IMD may then utilize the current telemetry communication context and/or the IMD device type information in connection with its power scaling routine.

The remaining tasks in IMD power adjustment process 700 were described above in the context of IMD power adjustment process 600; these tasks will not be redundantly described here in the context of process 700.

IMD power adjustment process 800 may begin by obtaining (task 802) contextual meaning information for data to be transmitted via telemetry communication from the IMD. In example embodiments, the IMD itself may dynamically generate the contextual meaning information, the IMD may receive the contextual meaning information from another device, or the IMD may retrieve stored contextual meaning information that was provided to the IMD during a setup or initialization procedure for the IMD. Task 802 may, for example, be performed during initialization of the telemetry session or prior to the telemetry session. Task 802 may also be performed periodically during the telemetry session.

The general characteristics and function of the contextual meaning information were explained in detail above. In example embodiments, the contextual meaning information may include, represent, or indicate a priority for the data to be transmitted by the IMD, a data type category for the data to be transmitted, and/or other information related to the function, purpose, operation, or use of the data to be transmitted. In this regard, IMD power adjustment process 800 may generate or indicate (task 804) a priority for the telemetry data, and/or generate or indicate (task 806) a data type category for the telemetry data. In practice, the IMD power characteristics can be adjusted in response to the priority, the data type category, or both. Consequently, the IMD may process these items in an appropriate manner in connection with its power scaling routine.

The remaining tasks in IMD power adjustment process 800 were described above in the context of IMD power adjustment process 600; these tasks will not be redundantly described here in the context of process 800.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

The invention claimed is:

1. An implantable medical device ("IMD") comprising:
    power scaling logic configured to process information pertaining to a telemetry communication device external to the IMD, and configured to generate scaling instructions in response to the information; and
    a transmitter coupled to the power scaling logic and configured to transmit telemetry signals, the transmitter having variable power characteristics; wherein
    the scaling instructions adjust the variable power characteristics of the transmitter.

2. An IMD according to claim 1, the variable power characteristics of the transmitter comprising output power of the transmitter.

3. An IMD according to claim 1, further comprising a receiver coupled to the power scaling logic and configured to receive telemetry signals, the receiver having variable power characteristics, wherein the scaling instructions adjust the variable power characteristics of the receiver.

4. An IMD according to claim 3, the variable power characteristics of the receiver comprising gain of receiver front end components of the IMD.

5. An IMD according to claim 1, the power scaling logic being configured to:
    determine, from the information pertaining to the telemetry communication device external to the IMD, a device type for the telemetry communication device; and
    generate the scaling instructions in response to the device type.

6. An IMD according to claim 5, wherein:
    the device type is indicative of a priority for telemetry communications between the IMD and the telemetry communication device; and
    the power scaling logic is configured to generate the scaling instructions in response to the priority.

7. An IMD according to claim 1, the power scaling logic being configured to:
    determine, from the information pertaining to the telemetry communication device external to the IMD, a telemetry range for the telemetry communication device; and
    generate the scaling instructions in response to the telemetry range.

8. An IMD according to claim 1, further comprising a receiver coupled to the power scaling logic and configured to receive a device identifier from the telemetry communication device, wherein the power scaling logic is configured to access the information using the device identifier.

9. An IMD according to claim 8, further comprising memory coupled to the power scaling logic, and configured to store a list of device identifiers for a number of telemetry communication devices that are compatible with the IMD.

10. An IMD according to claim 1, the power scaling logic being configured to:
    process IMD device type information for the IMD; and
    generate the scaling instructions in response to the IMD device type information.

11. An implantable medical device ("IMD") comprising:
    power scaling logic configured to process IMD device type information for the IMD, the IMD device type information being indicative of a present telemetry communication context for the IMD, and the power scaling logic being configured to generate scaling instructions in response to the IMD device type information; and
    a transmitter coupled to the power scaling logic and configured to transmit telemetry signals, the transmitter having variable power characteristics; wherein the scaling instructions adjust the variable power characteristics of the transmitter.

12. An IMD according to claim 11, the power scaling logic being configured to:
    process information pertaining to a telemetry communication device external to the IMD; and
    generate the scaling instructions in response to the information.

13. An IMD according to claim 11, wherein:
    the present telemetry communication context represents a configuration type for the IMD; and
    the power scaling logic is configured to generate the scaling instructions in response to the configuration type.

14. An IMD according to claim 11, wherein:
    the present telemetry communication context represents a priority for telemetry communications between the IMD and a telemetry communication device; and
    the power scaling logic is configured to generate the scaling instructions in response to the priority.

15. An IMD according to claim 11, wherein:
    the present telemetry communication context represents a telemetry range for the IMD; and
    the power scaling logic is configured to generate the scaling instructions in response to the telemetry range.

16. An IMD according to claim 11, wherein:
    the present telemetry communication context represents a present application mode for the IMD; and
    the power scaling logic is configured to generate the scaling instructions in response to the present application mode.

17. An IMD according to claim 11, the power scaling logic being configured to:
    obtain an IMD device identifier for the IMD; and
    access the IMD device type information using the IMD device identifier.

18. An IMD according to claim 11, the variable power characteristics of the transmitter comprising output power of the transmitter.

19. An IMD according to claim 11, further comprising a receiver coupled to the power scaling logic and configured to receive telemetry signals, the receiver having variable power characteristics, wherein the scaling instructions adjust the variable power characteristics of the receiver.

20. An IMD according to claim 19, the variable power characteristics of the receiver comprising gain of receiver front end components of the IMD.

21. An implantable medical device ("IMD") comprising:
    power scaling logic configured to process contextual meaning information associated with data to be transmitted by the IMD, and configured to generate scaling instructions in response to the contextual meaning information; and a transmitter coupled to the power scaling logic and configured to transmit telemetry signals, the transmitter having variable power characteristics; wherein the scaling instructions adjust the variable power characteristics of the transmitter.

22. An IMD according to claim 21, further comprising prioritization logic coupled to the power scaling logic, and configured to generate a priority for the data to be transmitted, wherein:

the contextual meaning information indicates the priority of the data; and the power scaling logic is configured to generate the scaling instructions in response to the priority.

23. An IMD according to claim 21, wherein:

the contextual meaning information indicates a data type category of the data to be transmitted; and the power scaling logic is configured to generate the scaling instructions in response to the data type category.

24. An IMD according to claim 23, further comprising memory coupled to the power scaling logic, and configured to store a list of data type categories for the IMD, the data type category being included in the list.

25. An IMD according to claim 21, the variable power characteristics of the transmitter comprising output power of the transmitter.

26. An IMD according to claim 21, further comprising a receiver coupled to the power scaling logic and configured to receive telemetry signals, the receiver having variable power characteristics, wherein the scaling instructions adjust the variable power characteristics of the receiver.

27. An IMD according to claim 26, the variable power characteristics of the receiver comprising gain of receiver front end components of the IMD.

28. An IMD according to claim 21, wherein the contextual meaning information is indicative of a type, function or purpose of the data to be transmitted by the IMD.

* * * * *